(12) United States Patent
Tverskoy

(10) Patent No.: US 10,342,486 B2
(45) Date of Patent: Jul. 9, 2019

(54) CLIP SENSOR DEVICE FOR MEASUREMENT OF VITAL SIGNS

(71) Applicant: Oxirate, Inc., Palo Alto, CA (US)

(72) Inventor: Boris Tverskoy, Palo Alto, CA (US)

(73) Assignee: OXIRATE, INC., Belmont, CA (US)

( * ) Notice: Subject to any disclaimer, the term of this patent is extended or adjusted under 35 U.S.C. 154(b) by 216 days.

(21) Appl. No.: 14/994,071

(22) Filed: Jan. 12, 2016

(65) Prior Publication Data

US 2016/0361016 A1   Dec. 15, 2016

Related U.S. Application Data

(63) Continuation of application No. 13/771,698, filed on Feb. 20, 2013, now abandoned.

(60) Provisional application No. 61/601,157, filed on Feb. 21, 2012.

(51) Int. Cl.
*A61B 5/00* (2006.01)
*A61B 5/1455* (2006.01)
*A61B 5/0205* (2006.01)

(52) U.S. Cl.
CPC .......... *A61B 5/6838* (2013.01); *A61B 5/0205* (2013.01); *A61B 5/14552* (2013.01); *A61B 5/6816* (2013.01); *A61B 5/6843* (2013.01)

(58) Field of Classification Search
CPC . A61B 5/02438; A61B 5/6838; A61B 5/0205; A61B 5/14552; A61B 5/6816; A61B 5/6843
USPC ................... 600/421, 310, 322–324
See application file for complete search history.

(56) References Cited

U.S. PATENT DOCUMENTS

| | | | | |
|---|---|---|---|---|
| 4,327,709 A | * | 5/1982 | Hanson | A61M 25/0111 600/18 |
| 4,685,464 A | * | 8/1987 | Goldberger | A61B 5/14552 600/344 |
| 5,217,012 A | * | 6/1993 | Young | A61B 5/02427 356/41 |
| 5,230,668 A | * | 7/1993 | Kawashima | F16G 5/20 474/263 |
| 6,353,750 B1 | * | 3/2002 | Kimura | A61B 5/0031 600/310 |
| 6,430,423 B2 | * | 8/2002 | DeLonzor | A61B 5/14552 600/310 |
| 6,491,647 B1 | * | 12/2002 | Bridger | A61B 5/021 128/900 |

(Continued)

*Primary Examiner* — Timothy J Neal
*Assistant Examiner* — Jae Woo
(74) *Attorney, Agent, or Firm* — Staniford Tomita LLP

(57) ABSTRACT

A clip sensor device for optical measuring vital signs of a subject is provided. The clip sensor device includes a internal supporting frame formed from an elongated plate configured to be folded into a desired orientation. A measuring probe is mounted on an upper surface of the frame. The measuring probe comprises a transmitter and receiver and configured for generating a time response of the blood perfused body tissue to the applied optical signal that is indicative of the vital signs of the subject. The clip sensor device also includes a pressing member mounted on the upper surface of the internal supporting frame. The pressing member includes one or more spring elements configured to provide a predetermined pressure on the blood perfused body tissue due to the deformation of the spring elements when said portion of blood perfused body tissue is applied against the pressing member.

20 Claims, 7 Drawing Sheets

(56) References Cited

U.S. PATENT DOCUMENTS

| | | | | |
|---|---|---|---|---|
| 7,187,960 B2* | 3/2007 | Abreu | ............... | A61B 5/01 |
| | | | | 374/E13.002 |
| 7,881,762 B2* | 2/2011 | Kling | ............... | A61B 5/14552 |
| | | | | 600/323 |
| 8,073,518 B2* | 12/2011 | Chin | ............... | A61B 5/14552 |
| | | | | 600/310 |
| 8,205,782 B2* | 6/2012 | Harari | ............... | A61B 17/0643 |
| | | | | 227/179.1 |
| 8,346,328 B2* | 1/2013 | Mannheimer | ............... | A61B 5/6843 |
| | | | | 600/310 |
| 8,700,116 B2* | 4/2014 | Schlottau | ............... | A61B 5/14551 |
| | | | | 600/310 |
| 2004/0260161 A1* | 12/2004 | Melker | ............... | A61B 5/0873 |
| | | | | 600/340 |
| 2007/0032716 A1* | 2/2007 | Raridan | ............... | A61B 5/14552 |
| | | | | 600/344 |
| 2007/0260130 A1* | 11/2007 | Chin | ............... | A61B 5/14552 |
| | | | | 600/323 |
| 2008/0091090 A1* | 4/2008 | Guillory | ............... | A61B 5/0478 |
| | | | | 600/301 |
| 2012/0078069 A1* | 3/2012 | Melker | ............... | A61B 5/0836 |
| | | | | 600/340 |
| 2014/0187885 A1* | 7/2014 | Kreuzer | ............... | A61B 5/02055 |
| | | | | 600/324 |

\* cited by examiner

CLIP SENSOR DEVICE FOR MEASUREMENT OF VITAL SIGNS

CROSS REFERENCE TO RELATED APPLICATIONS

This application is a continuation of U.S. patent application Ser. No. 13/771,698, filed Feb. 20, 2013, which claims the benefit of U.S. Provisional Patent Application No. 61/601,157 filed Feb. 21, 2012, each of which is herein incorporated by reference in its entirety.

FIELD OF THE INVENTION

This invention relates to medical techniques for monitoring vital signs, and in particular, to a device for measuring vital signs by detecting light transmitted or reflected from a blood perfused body tissue.

BACKGROUND OF THE INVENTION

It is well known in the art to use light transmitted through or reflected from a medium in order to determine characteristics of the medium. For example, in the medical field, where non-invasive physiological monitoring of vital signs of a patient is often required, light transmitted through a portion of the body, and reflected or scattered from the body surface may be measured to determine information about the patient.

For example, during surgery, blood pressure, heart rate, breathing rate and blood oxygen saturation are often monitored. Moreover, for some individuals, there may be a daily, even hourly need to measure such parameters to know the individuals health and/or to detect and treat some diseases.

Furthermore, information about vital signs can also be important to individuals involved in athletic training and physical exercising. For example, one of the important applications related to physical activity is continuous heart rate monitoring. This field still requires developments in a sense that a suppressive majority of nowadays optical sensors performing heart rate monitoring must be attached to body parts, which is inconvenient as well as relatively unreliable, mainly due to the dependency on motion-artifacts. Other kinds of related applications are related to blood pressure monitoring, oximetry, breathing rate monitoring, etc. Accordingly, the most common requirement for all of the corresponding monitoring devices is the ability to be stable, compact, sensitive and reliable under operation with batteries.

A number of optical monitoring techniques have been proposed in the art that use light as an optical signal transmitted through a medium, such as a portion of a blood perfused body tissue with the goal of determining vital signs. Generally, such a monitoring system (also known as a photoplethysmograph) includes a transmitter utilizing a probe clipped on a part of the body (e.g., a finger, forehead, ear pinna or an earlobe) that includes an optical source, e.g., a light emitting diode (LED) or a laser, for irradiating the body part with light placed on one side of the of the body part while a photodetector is placed on an opposite side of the body part.

The monitoring system also includes a receiver utilizing an optical photodetector (e.g., a photo diode) positioned in an optical path so that it has a field of view which ensures the capture of a portion of the light which is transmitted, reflected or scattered from the body part. The optical detector converts the light (i.e., optical signal) into an analog electrical signal, which is subsequently amplified and provided to an analyzer to retrieve information that was present in the optical signal.

An example of the medical monitoring device using light transmitted through a portion of the blood perfused body tissue is a pulse oximeter. Pulse oximetry is used to determine the oxygen saturation of arterial blood. Oxyhemoglobin mainly absorbs infrared light while deoxyhemoglobin mainly absorbs visible red light. Accordingly, pulse oximeter devices typically contain two types of light sources, either light emitting diodes or laser diodes, operating in the red band of light and in the infrared band of light, respectively. Pulse oximeter devices also include photo-detectors for each of above mentioned wavebands and the processing unit that detects the ratio of red/infrared absorption and calculates the patient's oxygen saturation of arterial blood.

Specifically, transmission of optical energy as it passes through the body is strongly dependent on the thickness of the material through which the light passes, or the optical path length. Many portions of a patient's body are typically soft and compressible. Therefore, when the patient moves, the thickness of material through which optical energy passes can change. This results in the changes of the optical path length. For example, if optical energy passes through a finger and the user of an optical device moves in a manner which distorts or compresses the finger, the optical path length changes. Changes in the optical path length together with the changes of venous blood movement through during motion can produce enough distortion in the measured signal to make it difficult or impossible to determine desired information.

For example, U.S. Pat. Appl. Pub. No. 2009/0227853 describes an ear hook plethysmography (PPG) sensor and/or pulse oximetry ($SpO_2$) sensor that can be attached to the skin in the regions of superficial artery and vein and posterior auricular artery and vein around the ear. For example, an ear wearable heart rate monitor can be constructed with these sensors.

U.S. Pat. No. 5,551,423 describes a pulse oximeter probe in the form of a clip that can be attached to an earlobe. The probe includes a pair of holding members that can be connected together at an end in such a way that they can pivot on a shaft. The holding members are arranged with a light-emitting device and a light-receiving device, in such a way that they are in a face-to-face relationship. The shaft is fitted with a leaf spring that urges the light-emitting and light-receiving devices to pivot in a direction in which they approach each other. The probe can be attached to an earlobe of a subject by holding the earlobe with the holding members.

It was noted that such an oximeter probe of the clip type has two major drawbacks. First, the holding members have to compress the earlobe so as to detect the pulsation of blood flowing in the compressed area but, then, the quantity of blood circulation decreases to lower the precision of measurement. Second, the probe which is attached to the earlobe is liable to movements and, hence, errors due to the movement of the earlobe are most likely to occur if measurements are done while the subject is walking.

To avoid these drawbacks, U.S. Pat. No. 5,551,423 providing a clip pulse oximeter probe that can be attached to the ear of a subject without compressing the site of measurement, and that is less sensitive to unwanted movements of the neck. The probe includes a pair of holding members pivotable on a shaft and configured for holding the basal part of the earlobe of a subject. The probe also includes a measuring section that consists of the light-emitting and light-receiving elements which are provided on the respective holding members in a face-to-face relationship. The compressing portions which hold the basal part of the earlobe are separated in position from the measuring section. One of the two holding members forms a bent portion at an end that can be inserted into the entrance to the auditory meatus, whereby the probe can be securely attached to the ear. In operation, the pulse oximeter probe detects the pulsation of blood in a blood vessel by reception of light at a light-receiving element after it is transmitted through a part of the earlobe.

SUMMARY OF THE INVENTION

Despite the known techniques in the area of measuring vital signs by detecting light transmitted or reflected from a portion of the blood perfused body tissue, there is a need for a novel sensor probe for robust measurement of vital signs of a subject (e.g., human) that can be used in two related areas, such as clinical use and everyday monitoring of the subject's physical activities. In both these areas, miniaturization of the measuring devices is required in order to fabricate them wireless and cost effective, so that these measuring devices could be deployed to a large population.

It would be advantageous to provide a stable miniature stand alone sensor for robust measurement of vital signs of the user that will be less vulnerable to motion artifacts under user's motion conditions such as running and exercising. Moreover, it would be advantageous if the system will be less vulnerable to optical coupling between the user's body and the light source as well as between the user's body and the photo-detector.

The present invention satisfies the aforementioned needs in the art by providing a novel clip sensor device for measuring vital signs of a subject. Example of the vital signs include, but are not limited to a heart rate, a heart rate variability, an arterial pulse waveform, a systolic blood pressure, a diastolic blood pressure, a mean arterial blood pressure, a pulse pressure, a breathing rate, a total hemoglobin content, and/or a blood oxygen saturation, etc. The clip sensor device includes an internal supporting frame formed from an elongated plate configured to be folded into a desired orientation. When desired, the internal supporting frame can include two plates connected by a wire or plurality of wires configured to be folded into a desired orientation.

A measuring probe mounted on the upper surface of the internal supporting frame and comprising a transmitter and receiver. The transmitter is configured for generating an optical signal and emitting the optical signal outwardly away from the upper surface of the internal supporting frame towards a portion of blood perfused body tissue of the subject. The receiver is configured for receiving light originated from the portion of blood perfused body tissue and generating a photo current signal including a time response of the blood perfused body tissue to the applied optical signal. The time response is indicative of the vital signs of the subject.

The clip sensor device also includes a pressing member mounted on the upper surface of the internal supporting frame. The pressing member comprises one or more spring elements configured to provide a predetermined pressure on the portion of the blood perfused body tissue due to the deformation of the spring element when the portion of blood perfused body tissue is applied against the pressing member.

According to some embodiments, the internal supporting frame is formed from a hard and formable material suitable to hold the clip sensor device into the desired orientation and maintain this orientation during operation of the clip sensor device.

According to an embodiment, the desired orientation is a U-shaped orientation.

According to some embodiments, the internal supporting frame is made from highly ductile and malleable metals.

According to an embodiment, the internal supporting frame is made from aluminum.

According to an embodiment, the internal supporting frame is made from steel.

According to an embodiment, thickness of the internal supporting frame is in the range of about 0.3 mm to about 0.8 mm.

According to an embodiment, the measuring probe is adjacent the left hand end of said internal supporting frame.

According to some embodiments, the transmitter includes at least one optical emitter. Examples of the optical emitter include, but are not limited to, a light emitting diode (LED) and laser diode. The optical emitter can, for example, operate in the red-near infrared spectral range, such as 600 nm through 1350 nm.

According to some embodiments, the receiver includes at least one optical detector. Examples of the optical detector include, but are not limited to, a PN photodiode, PIN photodiode, avalanche photodiode (APD), phototransistor, photothyristor, photomultiplier tube (PMT).

According to some embodiments, the transmitter and receiver are both mounted on the upper surface of the internal supporting frame adjacent either the right hand end or the left hand end of said internal supporting frame.

According to some embodiments, the transmitter is arranged at one end of the internal supporting frame, whereas the receiver is arranged at another end of the internal supporting frame.

According to some embodiments, the spring element(s) have a non-Hooke deformation behavior so that the extension or contraction of the spring element(s) does not have a linear dependence on the load applied to it.

According to some embodiments, the spring element(s) provide(s) a substantially constant force reaction when subjected to stress.

According to some embodiments, the spring element(s) include(s) a pad made from polyester foam or ribbon.

According to some embodiments, the spring element(s) include(s) a conical spring.

According to some embodiments, the measuring probe is adjacent one end of the internal supporting frame, whereas the pressing member is adjacent the opposite end of said internal supporting frame than the measuring probe.

According to some embodiments, the clip sensor device further includes a housing enveloping the at least the measuring probe by a covering sleeve, thereby to protect the measuring probe from damage.

According to some embodiments, the covering sleeve further envelopes at least a portion of the internal supporting frame.

According to some embodiments, the covering sleeve extends from the pressing member arranged at one end of the said internal supporting frame towards another end thereof.

According to some embodiments, the covering sleeve is made of a pliable padding material positioned on the upper and under surfaces surrounding the portion of the internal supporting frame extending from the pressing member until the right hand end, thereby encasing the measuring probe.

According to some embodiments, the covering sleeve includes at least one material selected from a soft rubber, plastic, a cloth.

According to some embodiments, the covering sleeve includes a window arranged over the measuring probe. The window is made of a material permeable to the radiation generated by the emitter.

According to some embodiments, the covering sleeve includes a plurality of V-shaped ribs arranged in the middle of the clip sensor device.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE PREFERRED EMBODIMENTS

Figure 1:
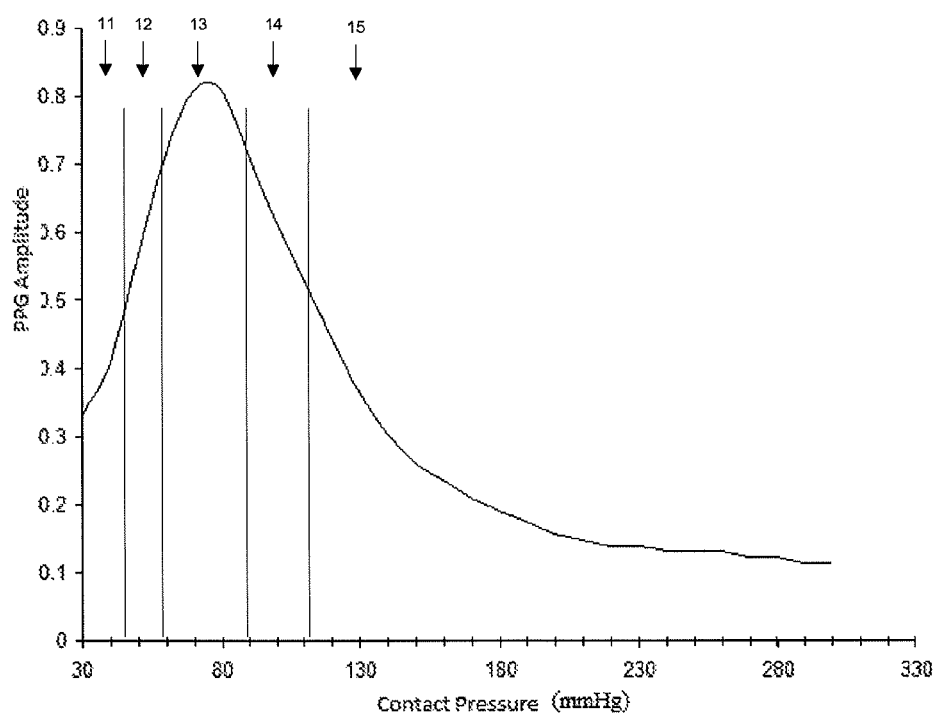
FIG. 1 illustrates an example of the dependency of an amplitude of a PPG signal on a contact pressure at the measurement location.

The principles and operation of the a clip sensor device for measurement of at least one vital sign of a human according to the present invention may be better understood with reference to the drawings and the accompanying description, it being understood that these drawings and examples in the description are given for illustrative purposes only and are not meant to be limiting. The same reference numerals and alphabetic characters will be utilized for identifying those components which are common in the device for measurement of at least one vital sign of a human and its components shown in the drawings throughout the present description of the invention.

As described above, photoplethysmographic sensors are typically placed on a subject in a location that is normally perfused with arterial blood to facilitate measurements of the desired vital signs. A photoplethysmographic (PPG) signal that is measured by a photoplethysmograph is a signal produced by arterial blood volume changes associated with periodic contractions and relaxations of the heart. A magnitude of the PPG signal is a function of the amount of the blood ejected from the heart with every systolic cycle, the optical absorption of blood, absorption by skin and tissue components, and the specific wavelengths used to illuminate the vascular tissue bed. During diastole, the blood volume in the vascular bed decreases, thus to increase the amount of the light transmitted or backscattered.

It should be noted that the reliability of the photoplethysmographic measurements depend on the contact pressure of a photoplethysmographic sensor on a measurement location. When the contact pressure used to secure the sensor to the measurement location on the body is too low, then distorted PPG waveforms can be generated, that results in inaccurate measurements. On the other hand, if the contact pressure is too high, then the blood circulation can be compromised or even necrosis can occur when the sensor is worn for extended periods of physical activity. When a blood circulation is slow, the ability to measure $SpO_2$ is also reduced. Moreover, when a too large contact pressure is used, a complete vessel occlusion can occur, that may lead to a complete loss of the PPG signal and jeopardize the ability to obtain $SpO_2$, HR and other vital sign data from the measurements. The optimal contact pressure will result in the greatest AC amplitudes and SNR will be the highest, which may result in improved measurement accuracy.

Referring to FIG. 1, an example of the dependency of an amplitude of a PPG signal on a contact pressure at the measurement location (such as a finger) is shown. The PPG amplitudes are normalized to the largest observed amplitude for each individual. Each point on the graph represents the mean normalized amplitude for all 10 individuals. The 95% confidence intervals were calculated for each point to determine if the observed amplitude was statistically within an optimal range, which was defined as pressures yielding normalized amplitudes greater than 0.7. A value of 0.7 was chosen as the nominal threshold because preliminary data suggested that this would be the maximal value that could be statistically identified without relying on extremely large samples greater than 150.

Regions 11 and 15 in FIG. 1 indicate contact pressures that do not provide optimal amplitudes. Regions 12 and 14 represent instances where the confidence interval produced amplitude values equal or less than 0.7, therefore, optimal amplitude in these regions is questionable. A region 13, corresponding to the pressure in the range of 60 mmHg-80 mmHg, represents optimal contact pressures.

In accordance with these experimental results, the present application provides a novel clip sensor device that can maintain the contact pressure at a desired magnitude. It should be note that the desired magnitude of the contact pressure may depend on the measurement location on the body of a subject. For example, when the measurements are carried out on a finger, the contact pressure can be in the range of 60 mmHg-80 mmHg Referring to FIG. 2, an exploded perspective view of a clip sensor device 20 for optic measuring at least one vital sign of a subject (e.g., a living human) is illustrated, according to one embodiment of the present invention. Examples of the vital signs which can be measured by the system of the present application include, but are not limited to, a heart rate, a heart rate variability, an arterial pulse waveform, a systolic blood pressure, a diastolic blood pressure, a mean arterial blood pressure, a pulse pressure, a breathing rate, a blood oxygen saturation, total hemoglobin content and/or anaerobic threshold monitoring, etc.

The clip sensor device 20 includes an internal supporting frame 21 formed, for example, from an elongated, relatively thin plate formed from any hard and formable materials suitable to hold the clip sensor device in a desired orientation. It should be understood that when desired the frame 21 can be formed from two plates 57, 56 at the ends 213 and 214 connected to each other by means of a wire or plurality wires. In particular, materials such as highly ductile and malleable metals, hard or firm plastic, and the like that can be bent into a tight U-shape and maintain this shape during operation can be used as materials suitable for the internal supporting frame 21. Examples of the metals suitable for internal supporting frame 21 include, but are not limited to, aluminum, copper, gold, steel, etc. In particular, when the internal supporting frame 21 is made of aluminum, it can have thickness in the range of 0.3 mm-0.8 mm. Such provision can make the frame 21 extremely light to minimize motion artifacts during operation of the clip sensor device 20.

Figure 2:
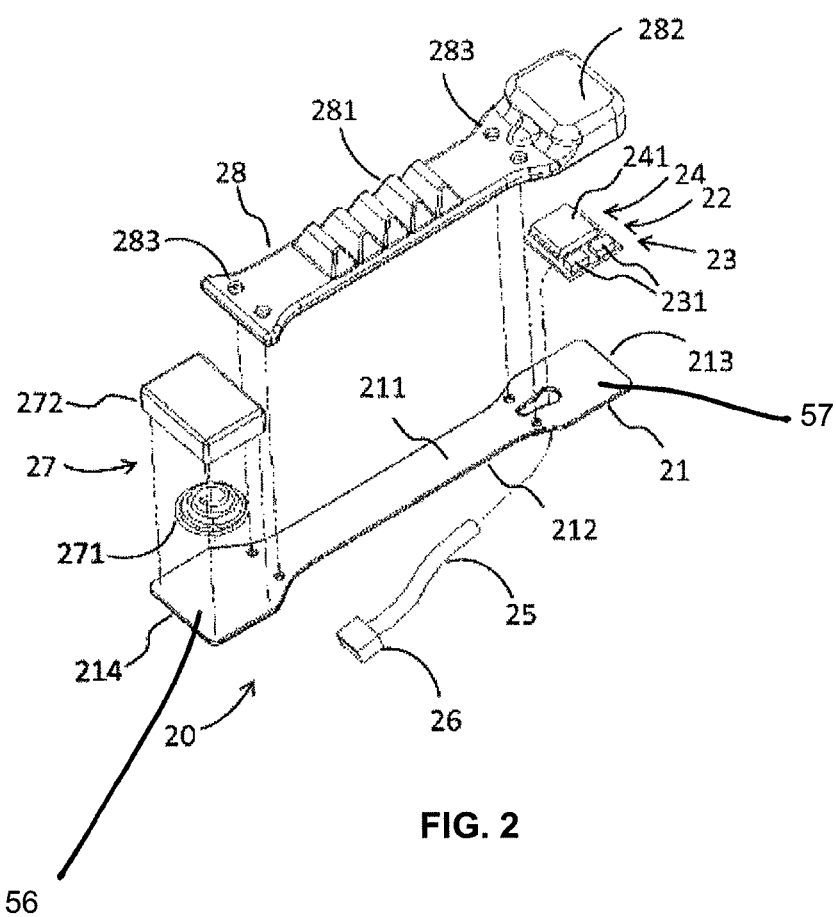
FIG. 2 illustrates an exploded perspective view of a clip sensor device for optic measuring at least one vital sign of a subject, according to one embodiment of the present application.

As shown in FIG. 2, the internal supporting frame 21 has an upper surface 211, an under surface 212, right hand end 213 and a left hand end 214. The terms "upper surface", "under surface", "right hand end", and "left hand end" are used herein for the purpose of description of a relationship between the different parts of the internal supporting frame 21 and the clip sensor device 20, rather than for description of orientation of the sensor structure in space.

The clip sensor device 20 also includes a measuring probe 22 mounted on the upper surface 211 of the internal supporting frame 21, adjacent the right hand end 213. According to one embodiment of the present invention, the measuring probe 22 comprises a transmitter 23 and a receiver 24. The transmitter 23 includes one or more optical emitters 231 (only two emitters are shown in FIG. 2) configured for generating an optical signal and emitting the optical signal outwardly away from the upper surface of the internal supporting frame 21. Generally, the emitter 231 can be a light source (e.g. visible, infrared, etc.), an ultra-sonic source, a microwave source, etc. Examples of the optical emitter 231 include, but are not limited to, emitting diodes (LEDs), laser diodes, or similar emitting devices.

Depending on the vital sign selected for determination, the optical sources may, for example, operate all at the same light wavelength. According to another embodiment, at least one of the light sources operates at a different wavelength. For example, for measurements of heart rate, one or more light emitting sources can operate at the same wavelength that can be selected within the transparency window of hemoglobin and water, i.e. in the red-near infrared spectral range, such as 600 nm through 1000 nm When the monitoring of total hemoglobin is targeted this range can be expanded till 1350 nm.

For measurements of a level of oxygen saturated in blood, at least two types of light emitting sources operating in the red band of light and in the infrared band of light are required.

According to one embodiment of the present invention, the receiver 24 includes one or more optical detectors 241 (only one optical detector is shown in FIG. 2) mounted on the upper surface 211 of the internal supporting frame 21, adjacent the right hand end 213. The optical detector 241 is arranged in the vicinity of the emitters 231 and configured for receiving light originated from (i.e., reflected from) at least a portion of the illuminated measurement location of the subject (not shown). In operation, the optical detector 241 generates a photo current signal that includes a time response of the blood perfused body tissue to the applied optical signal. The time response is indicative of vital signs of the subject. The optical detector 241 can include one or more photodiodes or other photo-receiving devices positioned in an optical path so that a field of view of the optical detector 241 ensures the capture of a portion of the light originated from the blood perfused body tissue. An example of the suitable photodiode includes, but is not limited to, a common low-cost PN photodiode, a PIN photodiode, an avalanche photodiode (APD), phototransistor, a photothyristor, a photomultiplier tube (PMT), etc. The receiver 24 may include an amplifier (not shown) coupled to the optical detector 241, and configured to convert the photocurrent generated by the optical detector 241 into a voltage signal carrying the information about the vital signs.

As shown in FIG. 2, the arrangement of the optical emitters 231 and the optical detector 241 with respect to the internal supporting frame 21 is such that the system 20 can operate with reflected light. However, when desired, the system 20 can also operate with transmitted light, mutatis mutandis.

Figure 3:
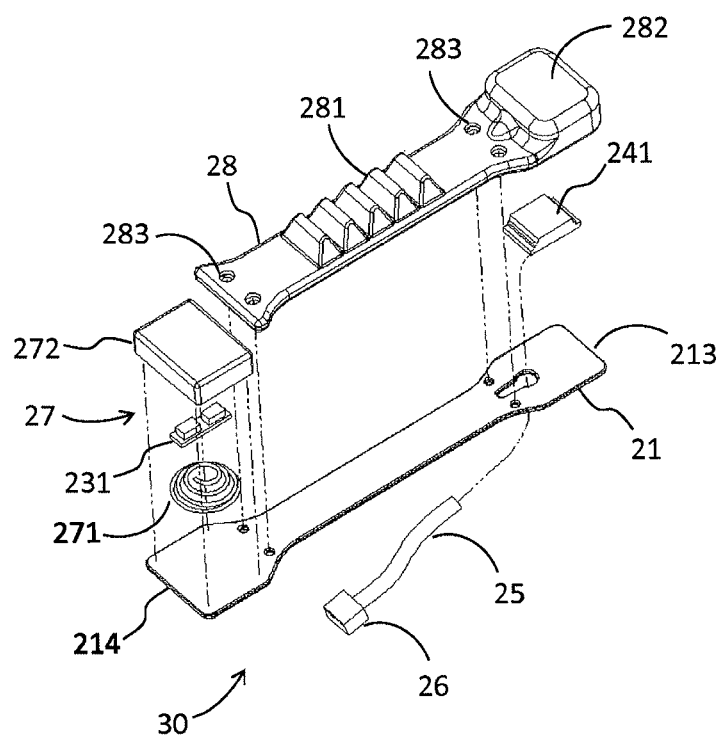
FIG. 3 illustrates an exploded perspective view of a clip sensor device for optic measuring at least one vital sign of a subject, according to another embodiment of the present application.

Referring to FIG. 3, an exploded perspective view of a clip sensor device 30 for optic measuring at least one vital sign of a subject is illustrated, according to another embodiment of the present invention. The clip sensor device 30 differs from the clip sensor device (20 in FIG. 2) in the fact that one or more optical emitters 231 are mounted at the right hand end 213 and one or more optical detector 241 is at the left hand end 214. It can be understood that this provision of the measuring probe enables operation with transmitted light.

The measuring probe 22 is electrically connected through a hard wired coupling 25 and optionally a connector 26 to external processing apparatus (not shown) that includes, inter alia, such modules as an optical signal driver (not shown) coupled to the transmitter 23 and configured for generating a series of electric pulses for driving the transmitter 23 by turning it "on" or "off". The external processing apparatus also includes a demodulator (not shown) and a control unit configured for adaptive control of the operation of the measuring probe 22. The processing apparatus can, for example, be associated with a suitably programmed computer system (not shown) having, inter alia, such known utilities as a processor, a memory unit for storing the processed data, and a monitoring system configured for presenting the measured results of vital signs. The processor is preprogrammed by a suitable software model capable of analyzing the received data and determining one or more desired vital signs. The monitoring system can include a display, printer and/or other monitoring devices (not shown). When desired, the monitoring system can include an alarm system to produce a human detectable signal when a vital sign measurement generated by the output unit meets predetermined criteria. For example, the monitoring system can be adapted to create a visual or audio alarm to alert a user that a detected vital sign is outside of a predetermined range. When desired the computer system can be associated with other computer system, which are connected to each other through a network, for example, through the Internet, thereby to transmit the measured information about the vital signs to a desired party.

The clip sensor device 20 also includes a pressing member 27 mounted on the upper surface 211 of the internal supporting frame 21, adjacent the left hand end 214, however other configurations are also contemplated. According to one embodiment of the present invention, the pressing member 27 comprises one or more spring elements 271, 272 configured to provide a predetermined pressing force on a surface against which the pressing member 27 is applied, due to the deformations of the spring elements 271, 272.

According to the present application the spring elements 271, 272 have a non-Hooke deformation behavior so that the extension or contraction of spring elements 271, 272 does not have a linear dependence on the force applied to it. According to an embodiment of the present invention, the spring elements 271 provide a relatively constant (or close to constant) force reaction when subjected to stress.

One type of a device with such properties is the spring element 272, which is in the form of a pad that is made, for example, from polyester foam or ribbon. Another type of device with such properties is the spring element 271, which is a conical spring, although other elements having non-Hooke deformation behavior are contemplated. For example, FIG. 2 shows a combined spring element that includes the conical spring element 271 embedded into the pad spring element 272 made of polyester foam.

Figure 4:
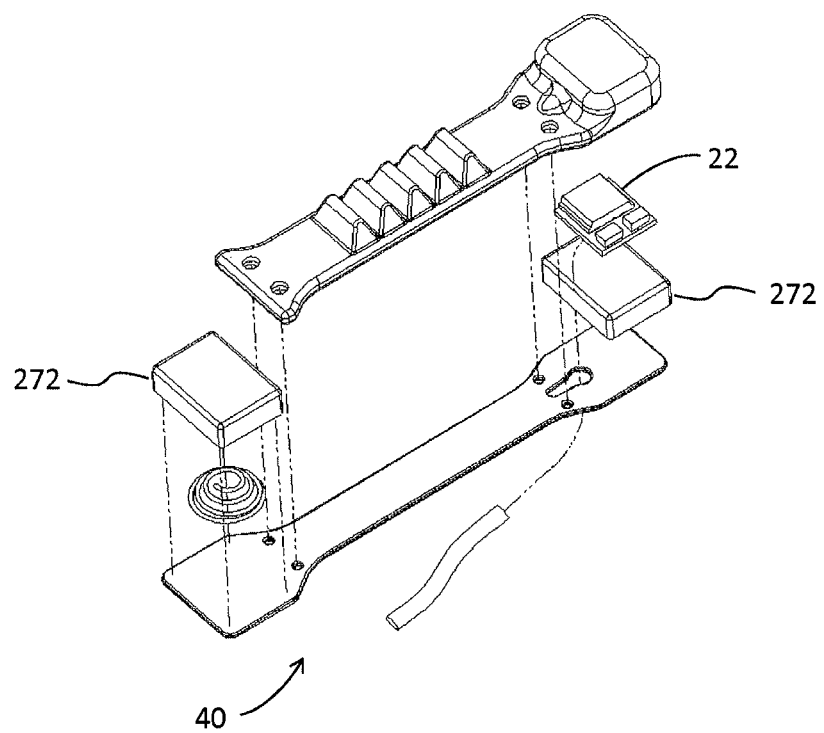
FIG. 4 illustrates an exploded perspective view of a clip sensor device for optic measuring at least one vital sign of a subject, according to yet another embodiment of the present application.

Referring to FIG. 4, an exploded perspective view of a clip sensor device 40 for optic measuring at least one vital sign of a subject is illustrated, according to another embodiment of the present invention. The clip sensor device 40 differs from the clip sensor device (20 in FIG. 2) in the fact that the spring elements 271, 272, mounted at the both ends 213 and 214 of the internal supporting frame 21, respectively. In this case, the measuring probe 22 can, for example, be arranged within the pad spring element 272 or mounted on the top of the spring element 271.

Figure 5A:
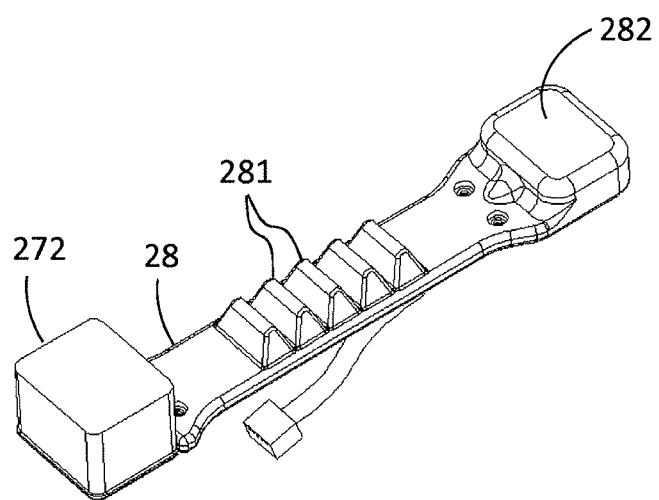
FIGS. 5A and 5B illustrate the clip sensor device according to one embodiment of the present application in the unfolded and U-shape folded configurations, correspondingly.
Figure 5B:
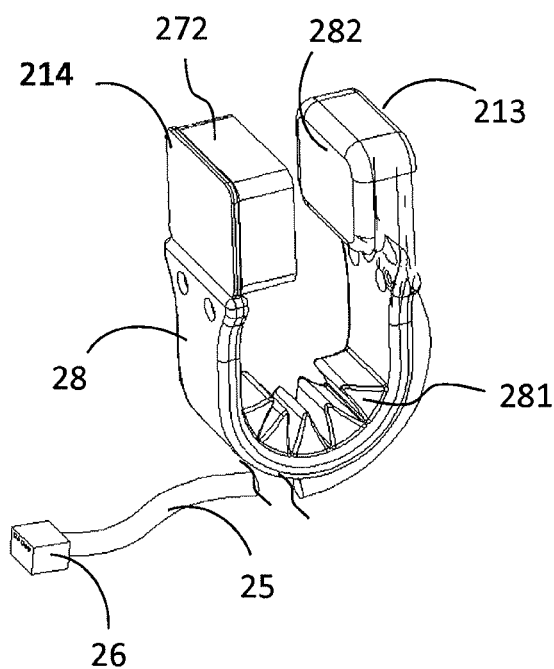
Figure 6:
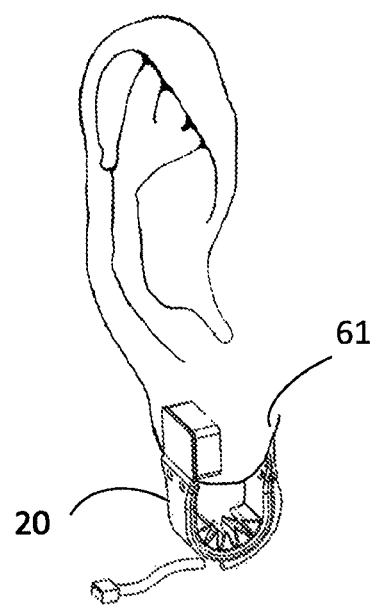
FIG. 6 illustrates an example of the clip sensor device of the present application attached to an earlobe.

FIGS. 5A and 5B illustrate the clip sensor device 20 in the unfolded and U-shape folded configurations. In operation, the internal supporting frame 21 is folded to form a generally U-shaped configuration. The clip sensor device 20 can be positioned by bending the internal supporting frame 21 over an anatomical location of the user's body (e.g., a finger, ear pinna, earlobe, lip, etc.) 51 with the blood perfused body tissue, and squeezing near the ends 213 and 214. An example of the clip sensor device 20 attached to an earlobe 61 is shown in FIG. 6.

In operation, the clip sensor device 20 clamps the anatomical location, the pressing member 27 is pressed against a blood perfused body tissue to exert an optimal pressure thereon over the squeezing range. According to some embodiments, the optimal pressure is within the range of 60 mmHg-80 mmHg As described above, the application of the optimal contact pressure will result in the greatest PPG amplitudes and provide an enhance measurement accuracy.

Referring to FIGS. 2, 5A and 5B together, the clip sensor device 20 can also include a housing 28 enveloping the measuring probe 22. The housing 28 can be in the form of a covering sleeve to protect the measuring probe 22 from damage owing to humidity, scratching, contacts with foreign objects, and other damaging factors during exploitation. When desired, at least a portion of the internal supporting frame 21 can also be enveloped by the housing (i.e., covering sleeve) 28. As shown in FIG. 2, the covering sleeve 28 extends from the pressing member 27 towards the right hand end 213. The covering sleeve 28 is made of a pliable padding material positioned on the upper and under surfaces 211 and 212 surrounding the portion of the internal supporting frame 21 extending from the pressing member 27 until the right hand end 213, thereby encasing the measuring probe 22, and provides a conformable surface for engagement of the clip sensor device 20 with the measurements location of the subjects body. The covering sleeve 28 can be made from or include, for examples, a soft rubber, plastic, (such as silicon or polyurethane), cloth and other materials. When desired, the housing (i.e., covering sleeve) 28 can be fixed to the internal supporting frame 21 by means of bolts, screws and or rivets (not shown) via openings 283.

According to an embodiment, the covering sleeve 28 includes a window 282 arranged over the measuring probe 22 made of a material (e.g., glass crystal) permeable to the radiation generated by the emitter 231 and to the radiation originated from the blood perfused body tissue for collecting by the detector 241.

According to an embodiment, the covering sleeve 28 includes a plurality of V-shaped ribs 281 arranged in the middle of the clip sensor device 20. As shown in FIG. 5A, the V-shaped ribs 281 prevent the frame from bending in V-shape and force it to bend in U-shape protecting the frame from folding it into V-shape. It should be understood that when a frame receives a V-shape during folding, it can be broken quicker than in the case when the frame receives U-shape, since U-shape is less acute and can be folded much larger times before breaking apart.

Those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

When desired, the clip sensor devices 20, 30 and 40 can be in the form of a jewelry ring, jewelry ear clip or any other jewelry item, and have an attractive ornamental appearance. When desired, the clip sensor devices can be decorated with gemstones, crystals and/or other decorating items.

Also, it is to be understood that the phraseology and terminology employed herein are for the purpose of description and should not be regarded as limiting.

Finally, it should be noted that the word "comprising" as used throughout the appended claims is to be interpreted to mean "including but not limited to".

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

What is claimed is:

1. A clip sensor device for optical measuring at least one vital sign of a subject, the clip sensor device comprising:
   an internal supporting frame made of a malleable material configured to be folded into a U-shaped orientation and unfolded into an unfolded orientation, and having an upper surface, an undersurface, a right hand end, and a left hand end;
   a measuring probe mounted on the upper surface of one end of the internal supporting frame and comprising a transmitter configured for generating an optical signal and emitting the optical signal outwardly away from the upper surface of the internal supporting frame towards a portion of blood perfused body tissue of the subject, and a receiver configured for receiving light originated from the portion of blood perfused body tissue and generating a photo current signal including a time response of the blood perfused body tissue to the applied optical signal, the time response is indicative of said at least one vital sign of the subject;

a pressing member mounted on the upper surface of a second end of the internal supporting frame opposite the a first end, said pressing member comprising at least one spring element configured to provide a predetermined pressure on the portion of the blood perfused body tissue due to the deformation of the spring element when the internal supporting frame is folded into the U-shaped orientation and opposite sides of the portion of blood perfused body tissue are compressed between the right hand end and the left hand end of the internal supporting frame.

2. The clip sensor device of claim 1, wherein said internal supporting frame includes a hard and formable material suitable to hold the clip sensor device into said desired orientation and maintain this orientation during operation of the clip sensor device.

3. The clip sensor device of claim 1, wherein said desired orientation is a U-shaped orientation.

4. The clip sensor device of claim 1, wherein said internal supporting frame is made from highly ductile and malleable metals.

5. The clip sensor device of claim 1, wherein said internal supporting frame is made from a metal selected from aluminum, steel, copper and gold.

6. The clip sensor device of claim 1, wherein the transmitter includes at least one optical emitter selected from a light emitting diode (LED) and laser diode.

7. The clip sensor device of claim 6, wherein said at least one optical emitter operates in the red-near infrared spectral range, such as 600 nm through 1350 nm.

8. The clip sensor device of claim 1, wherein the receiver includes at least one optical detector selected from a PN photodiode, a PIN photodiode, an avalanche photodiode (APD), a phototransistor, a photothyristor, a photomultiplier tube (PMT).

9. The clip sensor device of claim 8, wherein said at least one optical emitter and said at least one optical detector are both mounted on the upper surface of the internal supporting frame adjacent either the right hand end or the right hand end of said internal supporting frame.

10. The clip sensor device of claim 1, wherein the transmitter is arranged at one end of the internal supporting frame, whereas the receiver is arranged at another end of the internal supporting frame.

11. The clip sensor device of claim 1, wherein said at least one spring element have a non-Hooke deformation behavior so that the extension or contraction of said at least one spring element does not have a linear dependence on the force applied to it.

12. The clip sensor device of claim 1, wherein said at least one spring element provides a substantially constant force reaction when subjected to stress.

13. The clip sensor device of claim 1, wherein said at least one spring element includes a pad made from polyester foam or ribbon.

14. The clip sensor device of claim 1, wherein said at least one spring element includes a conical spring.

15. The clip sensor device of claim 1, wherein said measuring probe is adjacent one end of said internal supporting frame, whereas said pressing member is adjacent the opposite end of said internal supporting frame than the measuring probe.

16. The clip sensor device of claim 1, further comprising a housing enveloping the at least the measuring probe by a covering sleeve, thereby to protect the measuring probe from damage.

17. The clip sensor device of claim 16, wherein the covering sleeve further envelopes at least a portion of the internal supporting frame.

18. The clip sensor device of claim 16, wherein the covering sleeve extends from the pressing member arranged at one end of the said internal supporting frame towards another end thereof.

19. The clip sensor device of claim 16, wherein the covering sleeve includes a window arranged over the measuring probe made of a material permeable to the radiation generated by the emitter.

20. The clip sensor device of claim 16, wherein the covering sleeve includes a plurality of V-shaped ribs arranged in the middle of the clip sensor device.

\* \* \* \* \*